United States Patent [19]
Evans et al.

[11] Patent Number: 5,104,319
[45] Date of Patent: Apr. 14, 1992

[54] METHOD OF MANUFACTURING DENTAL RESTORATIONS

[76] Inventors: Philip A. Evans, 12 Methley Drive, Leeds, England, LS7 3NE; Paul Harrison, 11 Rochester Terrace, Leeds, England, LS6 3DF

[21] Appl. No.: 561,771

[22] Filed: Aug. 2, 1990

[30] Foreign Application Priority Data

Aug. 9, 1989 [GB] United Kingdom ............... 8918178

[51] Int. Cl.⁵ .................. A61C 13/08; A61C 5/00; A61C 5/10
[52] U.S. Cl. .................. 433/202.1; 433/215; 433/223
[58] Field of Search .................. 433/202.1, 215, 223

[56] References Cited

U.S. PATENT DOCUMENTS 4,556,389 12/1985 Veno et al. ..................... 433/206
4,937,928 7/1990 Van der Zel ..................... 433/223
4,957,440 9/1990 Hankins et al. ................... 433/201.1

FOREIGN PATENT DOCUMENTS 56-14295 of 1981 Japan.

Primary Examiner—Cary E. O'Connor
Assistant Examiner—Cindy A. Cherichetti
Attorney, Agent, or Firm—Klauber & Jackson

[57] ABSTRACT

A method for the production of full or partial dental restorations including veneers, crowns, inlays, onlays, and bridge structures, and dental restorations produced by the method. The method utilizes the technique of flame spraying to form a basal layer of a technical ceramic based material upon which porcelains are applied to produce a strong, aesthetically acceptable and custom made dental restoration. The technical ceramic based material may be Alumina, Zirconia, Titania, or combinations thereof, and the flame spraying may be a direct method or an indirect method. The technical ceramic based material may include small amounts of silicate based materials.

10 Claims, 1 Drawing Sheet

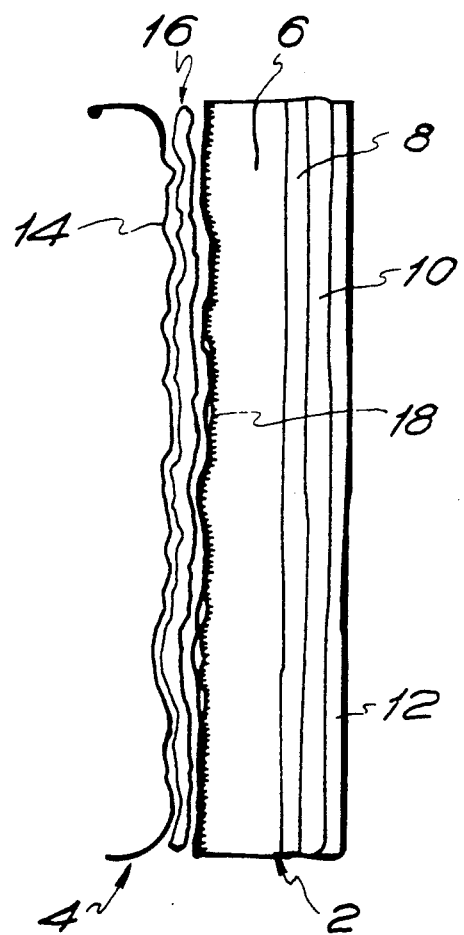

METHOD OF MANUFACTURING DENTAL RESTORATIONS

This invention relates to the fabrication of full or partial dental restorations, including veneers, crowns, inlays, onlays, and bridge structures, hereinafter referred to as dental restorations.

The invention utilises the technique of flame spraying to produce a relatively dense basal layer of a technical ceramic based material which firstly acts as a permanent form upon which porcelain can be applied in order to yield ultimate aesthetics of the restoration, and which secondly serves to strengthen the restoration and provide a means for bonding the restoration to a prepared tooth in which the contribution made by the mechanical bonding mechanism is enhanced.

The invention overcomes the problems of shrinkage and subsequent loss of fit traditionally associated with the application of technical based ceramic materials to produce custom made dental restorations.

Ceramic materials in the form of porcelains have been used and developed since the turn of the century. For example, in 1900 Ernsmere reported that Charles Land had developed a technique of fabricating jacket crowns on platinum foil matrices utilising porcelain as a restorative material, and although these original all-porcelain jacket crowns were considered to be aesthetically acceptable, they were weak in tension and flexion and were thus prone to breakage during clinical service. In an effort to overcome this problem, much of the development of dental ceramics has addressed itself to the need to increase the strength of dental restorations in order to provide adequate clinical performance.

Advances in dentine and enamel bonding resin technology have led to the possibility of applying dental restorations of thinner section, thus increasing the need for greater inherent strength in restorations.

In order to enhance the strength of dental restorations, it has been common practice to employ the ceramo-metal technique. U.S. Pat. Nos. 3,052,982 and 3,052,983 to Weinstein et al disclose specific compositions and fabrication conditions of porcelains for bonding to metals, and the U.S. Pat. No. 3,819,366 to Katz and the U.S. Pat. No. 3,961,420 to Tuccillo both disclose details of ceramo-metal dental restorations incorporating gold palladium silver and improved white gold alloys respectively. The ceramo-metal technique has traditionally been employed for use with crown and bridge type restorations, and although such restorations display satisfactory strength properties they have the disadvantage that they cannot be considered to be conservative of tooth tissue; also, they require the use of opaque porcelain to mask out the underlying metal structure.

Japanese Patent No. 81 014295B to Sumitomo discloses the plasma spraying technique for use in the manufacture of dental crowns, but it is noted that the disclosure in the Sumitomo patent involves the application of metallic, metallic-ceramic mixtures and technical based ceramic materials in the masking out of a metallic substructure prior to the application of dentine and enamel porcelains. The technique represents a substitution of these materials for the opaque porcelain layer. The present invention represents the use of the flame spraying technique to form a basal layer of a technical ceramic based material alone which ultimately exists as a structure in its own right and not as a coating on a metal substructure or substrate.

A proposal similar to Sumitomo is disclosed in U.S. Pat. No. 4,937,928 to van der Zel. The patent to van der Zel discloses a method for making a dental crown by means of a CAD-CAM system, the method involving the application of a metal layer to a model of the dental preparation, the metal layer being ground back to the desired shape and thickness under the control of the CAD-CAM system. Thereafter, layers of porcelain are applied to the metal base layer to provide the finished dental crown. In van der Zel, the metal base layer is provided because porcelain on its own would not provide sufficient and adequate strength for long-term function of the dental crown.

In 1968, United Kingdom Patent No. 1 105 111 to McLean et al proposed that improvements in the strengths of porcelains themselves could be afforded by the introduction of aluminous porcelains. This represented the introduction of the technical ceramic based material Alumina as a strengthening, particulate, second phase into a porcelain matrix. Such strength improvements however have not been sufficient to allow the manufacture of dental restorations such as posterior crowns and bridges. McLean et al subsequently disclosed, in United Kingdom Patent No. 1 483 362, a method for improving the strength of dental crowns by the bonding of a platinum foil to the inner fitting surface of the aluminous porcelain, but this method is not at all suited to the fabrication of aesthetically acceptable thin sections due to the necessity of masking out the metal.

More recently, U.S. Pat. Nos. 3,732,087, 4,189,325 and 4,515,634 to Grossman, Barret et al, and Wu respectively, introduced systems utilising glass-ceramic, and U.S. Pat. No. 4,265,669 to Starling et al introduced a system utilising a non-shrink ceramic, but such systems have not been widely accepted and commonly have had problems associated with aesthetics, particularly where in-situ alterations have to be conducted involving the removal of surface stain/glaze areas.

A fluormica based glass-ceramic material known as DICOR has been used to form a basal layer in the manufacture of a WILLI'S crown, but the strengths of such glass-ceramic materials are only equivalent to the aluminous porcelains above referred to. Decreases in strength are also known to occur if the surface layer of crystallisation is removed or damaged. For these reasons, such materials are not though to be suitable for use in the manufacture of acceptable thin sections.

Methods have been disclosed, for example in U.S. Pat. No. 4,473,353 to Greggs and in U.S. Pat. No. 4,579,530 to McLaughlin, for the manufacture of a thin section all-porcelain veneer type restoration to cover anterior teeth.

The patent to Greggs discloses the application of porcelain onto a platinum foil, and the patent to McLaughlin discloses the application of porcelain onto a suitable refractory investment model, and whilst such thin-section all-porcelain, veneer type restorations are finding increasing application, they do however suffer from breakage on placement due to relatively low strength.

The disclosure by Faunce in his U.S. Pat. No. 3,986,261 of the use of a pre-formed, fully polymerised, plastics material as a veneer facing with uniform colour throughout its sectional thickness has been improved somewhat more recently. In this more recent disclosure, U.S. Pat. No. 4,433,959 to Faunce allows for the lamination of the veneer facing using other resins, glass, and ceramic or glass-ceramic resin composite materials, or combinations thereof, to afford aesthetics which more closely match normal human tooth tissue. Further, the disclosure refers to the laminar structure having an outer layer which is dense and relatively hard in order to prevent the discolouration which is associated with relatively porous polymers, whilst the inner layer is less dense, porous or cellular in structure, in order to promote efficient bonding to the labial surface of the tooth. This inner surface or layer in one form can be manufactured by the electrostatic spraying of microcrystalline particles which are subsequently sprayed with one or more layers of resin which flow around the particles to form a smooth surface.

The present invention on the other hand provides a high temperature flame spraying technique which forms a relatively dense technical ceramic based layer which is rough on the microscale. This type of surface enhances the contribution made by a mechanical bonding mechanism, in bonding such a dental restoration incorporating such technology, to a prepared tooth. The present invention is applicable to the fabrication of basal layers of technical ceramic based materials for all types of dental restorations and is not restricted to the labial face.

According to a first aspect of the present invention there is provided a method for use in the manufacture of a dental restoration including the step of forming a base layer of predetermined thickness of said restoration by flame spraying.

The flame spraying may be a direct flame spraying technique or an indirect flame spraying technique.

The flame spraying will preferably utilise a free flowing powder or liquid which incorporates a technical ceramic based material. Said technical ceramic based material will preferably be Alumina, Zirconia, or Titania, or combinations thereof.

The method will include the additional step of applying a plurality of layers of porcelain to the said base layer.

According to a second aspect of the present invention there is provided a dental restoration including a base layer of predetermined thickness formed by flame spraying.

The said base layer will preferably be composed of a technical ceramic based material.

The dental restoration will preferably include a plurality of layers of porcelain carried by said base layer.

In order that the invention may be more readily understood, an embodiment thereof will now be described, by way of example, reference being made to the accompanying drawing, the single FIGURE of which is a cross-sectional elevation of a dental restoration in accordance with the invention.

Referring to the drawing, there is shown a section of a dental restoration indicated generally by reference numeral 2, and positioned in relation to a natural tooth 4.

As will be seen, the dental restoration 2 comprises a base layer 6 of a technical ceramic based material such as, for example, Alumina, Zirconia, or Titania, or combinations thereof, and subsequent layers 8, 10, and 12 of dental porcelains which are applied to the base layer to enhance the aesthetics of the restoration.

The base layer 6 is formed by a flame spraying technique which includes plasma spraying and detonation gun methods of application, and the dental restoration 2 is applied to the natural tooth 4 through the intermediary of a layer 16 of a bonding agent. Prior to the application of the dental restoration to the natural tooth 4, treatment of the tooth surface 14 may be necessary—depending upon which bonding material is used—such treatment involving the use of the phosphoric acid etching technique.

The flame spray process used in the method of the invention utilises a free flowing powder or liquid which incorporates a technical ceramic based material such as Alumina, Zirconia, or Titania, or combinations thereof. The free flowing powder or liquid is introduced into the flame/plasma whereupon it is given kinetic energy and thermal energy and directed at the target, i.e. a tooth positive, which will have been formed by casting a refractory type material into an initial polymer impression which incorporates the tooth to be restored.

The rate of spraying is controlled by the design of the nozzle in the flame spray gun and the pressure of the fuel gas used.

Swift passes are made so as to deposit the technical ceramic based material onto the tooth positive target in a series of successive layers. This action serves to facilitate the fabrication of a relatively dense microstructure.

Small amounts of silicate based materials may be added to the pre-cursor feed materials to facilitate the production of a fully dense technical ceramic based material layer.

It should be noted that, dependent upon the type of technical ceramic based material used and the end result that is required, post-flame spray heat treatment of the base layer 6 may be necessary prior to the application of the layers of porcelain, not only to fully densify the base layer but also to homogenise alloying additions or phases present and to enhance the optical properties of the base layer 6.

Due to the nature of the microstructure produced following flame spraying, any small amount of remaining shrinkage of the layer is promoted throughout the depth of the layer, thus not affecting the fit of the final dental restoration.

Utilising the optimum conditions outlined, a base layer 6 approaching theoretical density can be produced. The finished thickness of the base layer 6 will be dependent upon which type of dental restoration is being manufactured and may vary from a single particulate layer in the order of 1 micro-meter to a substantial layer in the order of 3 millimeters.

The flame spray process used to produce the base layer 6 may be a 'direct' technique or it may be an 'indirect' technique. The 'direct' technique involves flame spraying directly onto a refractory tooth positive target. The 'indirect' technique involves burnishing a thin layer of platinum foil over the refractory tooth positive and then flame spraying onto this foil. The platinum foil serves to facilitate the removal of the technical ceramic based material base layer 6 from the refractory tooth positive, following the furnace heat treatments involved with the application of the porcelain layers 8, 10, and 12. Use of the 'direct' technique necessitates removal of the refractory material from the base layer 6 following the application of the porcelain layers.

Following the formation of the base layer 6 as above related, conventional techniques are used for the application of the layers 8, 10, and 12 of the dental porcelains.

The first layer 8 of porcelain must have a co-efficient of thermal expansion which is matched to, or preferably lower than, that of the technical ceramic based material base layer 6. A porcelain having this slightly lower co-efficient of thermal expansion will be placed into slight compression upon cooling, thus yielding a dental restoration with optimum strength properties and aesthetics.

A dental restoration incorporating a base layer 6 produced in accordance with the invention has excellent shape retention, since the normally large shrinkages (15 to 20 vol %) experienced on sintering a technical ceramic formed by casting or die pressing techniques are greatly reduced or overcome. The strength of the dental restoration produced in accordance with the invention is greater than similar dental restorations which are manufactured from porcelain based materials.

In addition, the surface area for the bonding of the dental restoration to the natural tooth is increased due to the mainly crystalline nature of the technical ceramic based material. Pre-treatment of the surface 18 of the base layer 6 may be carried out with an agent designed to enhance bond strength. Such treatment involves the application of a silane bond coating.

Finally, satisfactory aesthetics can be produced by a combination of materials and process variations which take account of hue, value, chroma, translucency, shape, outline form, contour, proportion and soft tissue harmony with the oral cavity.

What is claimed is:

1. A method for use in the manufacture of a dental restoration including the step of forming, by flame spraying, a base layer of technical ceramic based material of a predetermined thickness of said restoration.

2. A method in accordance with claim 1, wherein the flame spraying is a direct technique.

3. A method in accordance with claim 1, wherein the flame spraying is an indirect technique.

4. A method in accordance with claim 1, wherein the flame spraying utilises a free flowing material which incorporates said technical ceramic based material.

5. A method in accordance with claim 4, wherein the technical ceramic based material is selected from the group consisting of Alumina, Zirconia, Titania, and combinations thereof.

6. A method in accordance with claim 4, wherein the free flowing material includes small additions of silicate based materials.

7. A method in accordance with claim 1, including the additional step of applying to said base layer of technical ceramic based material a plurality of layers of porcelains.

8. A dental restoration including a base layer of technical ceramic based material of predetermined thickness of said restoration, said base layer of technical ceramic based material being formed by flame spraying.

9. A dental restoration in accordance with claim 8, wherein said technical ceramic based material includes small additions of silicate based materials.

10. A dental restoration in accordance with claim 8, wherein said restoration includes a plurality of layers of porcelain carried by said base layer.

* * * * *